United States Patent
Afroz et al.

(10) Patent No.: US 10,278,629 B2
(45) Date of Patent: May 7, 2019

(54) IMPLANTABLE BIOCOMPATIBLE SIC SENSORS

(71) Applicants: UNIVERSITY OF SOUTH FLORIDA, Tampa, FL (US); MISSISSIPPI STATE UNIVERSITY, Starkville, MS (US)

(72) Inventors: Shamima Afroz, Tampa, FL (US); Sylvia Wilson Thomas, Orlando, FL (US); Stephen E. Saddow, Odessa, FL (US); Gokhan Mumcu, Tampa, FL (US); Erdem Topsakal, Starkville, MS (US)

(73) Assignees: University of South Florida, Tampa, FL (US); Mississippi State University, Starkville, MS (US)

( * ) Notice: Subject to any disclaimer, the term of this patent is extended or adjusted under 35 U.S.C. 154(b) by 1051 days.

(21) Appl. No.: 14/383,967

(22) PCT Filed: Mar. 12, 2013

(86) PCT No.: PCT/US2013/030362
§ 371 (c)(1),
(2) Date: Sep. 9, 2014

(87) PCT Pub. No.: WO2013/138275
PCT Pub. Date: Sep. 19, 2013

(65) Prior Publication Data
US 2015/0051466 A1    Feb. 19, 2015

Related U.S. Application Data

(60) Provisional application No. 61/609,546, filed on Mar. 12, 2012.

(51) Int. Cl.
*A61B 5/1473*    (2006.01)
*A61B 5/00*    (2006.01)
(Continued)

(52) U.S. Cl.
CPC .......... *A61B 5/1473* (2013.01); *A61B 5/0002* (2013.01); *A61B 5/053* (2013.01);
(Continued)

(58) Field of Classification Search
CPC .......... A61B 2562/125; A61B 5/14532; A61B 5/0031; A61B 5/686
See application file for complete search history.

(56) References Cited

U.S. PATENT DOCUMENTS

| 5,165,407 A | 11/1992 | Wilson et al. |
| 5,728,281 A | 3/1998 | Holmstrom et al. |

(Continued)

FOREIGN PATENT DOCUMENTS

| ES | 2278508 | 8/2007 |
| WO | 0077886 | 12/2000 |

OTHER PUBLICATIONS

Yakimova et al., Surface functionalization and biomedical applications based on SiC, Journal of Physics D: Applied Physics, p. 6435-6442, Oct. 5, 2007.*

(Continued)

*Primary Examiner* — Puya Agahi
(74) *Attorney, Agent, or Firm* — Thomas | Horstemeyer, LLP (57) ABSTRACT

In one embodiment, an implantable biosensor includes a sense antenna comprising a silicon carbide substrate and a radiating electrode formed on the substrate.

6 Claims, 7 Drawing Sheets

(51) Int. Cl.

| | |
|---|---|
| A61B 5/053 | (2006.01) |
| A61B 5/07 | (2006.01) |
| A61B 5/145 | (2006.01) |
| H01Q 9/04 | (2006.01) |
| H01Q 1/38 | (2006.01) |

(52) U.S. Cl.
CPC .......... *A61B 5/076* (2013.01); *A61B 5/14532* (2013.01); *A61B 5/686* (2013.01); *H01Q 1/38* (2013.01); *H01Q 9/0407* (2013.01); *A61B 5/0031* (2013.01); *A61B 2562/125* (2013.01); *A61B 2562/18* (2013.01)

(56) References Cited

U.S. PATENT DOCUMENTS

| | | | |
|---|---|---|---|
| 6,624,510 B1 * | 9/2003 | Chan ................ | A61B 5/04001 257/734 |
| 7,613,491 B2 | 11/2009 | Boock et al. | |
| 7,811,231 B2 | 10/2010 | Jin et al. | |
| 7,828,728 B2 | 11/2010 | Boock et al. | |
| 2002/0049394 A1 * | 4/2002 | Roy ...................... | A61B 5/4504 600/594 |
| 2005/0107677 A1 | 5/2005 | Ward et al. | |
| 2006/0258761 A1 | 11/2006 | Boock et al. | |
| 2007/0276201 A1 * | 11/2007 | Lee ...................... | A61B 5/0031 600/301 |
| 2007/0282172 A1 * | 12/2007 | Toumazou ............ | A61B 5/0031 600/300 |
| 2008/0033260 A1 * | 2/2008 | Sheppard ................ | A61N 1/05 600/301 |
| 2008/0079565 A1 * | 4/2008 | Koyama ............... | A61B 5/0031 340/539.12 |
| 2009/0043183 A1 * | 2/2009 | Kermani .............. | A61B 5/0031 600/365 |
| 2010/0258919 A1 | 10/2010 | Makarov | |
| 2010/0298679 A1 | 11/2010 | Wu et al. | |
| 2011/0137184 A1 * | 6/2011 | Ren ....................... | G01L 9/0098 600/485 |
| 2013/0231550 A1 * | 9/2013 | Weinstein ............ | A61B 5/0028 600/407 |

OTHER PUBLICATIONS

Naji, et al., Cytocompatibility of two coating materials, amorphous alumina and silicon carbide, using human differentiated cell cultures; INSERM U. Biomaterials 1991, vol. 12.
Saddow, et al., Single-crystal silicon carbide: a biocompatible and hemocompatilbe semiconductor for advanced biomedical applications; Mater. Res. Soc. Symp. Proc., vol. 1246, 2010.
Atanasov, et al., "Biosensor for Continuous Glucose Monitoring", Dept. of Chemical and Nuclear Engineering, University New Mexico, Jun. 3, 1993.
Shults, et al., "A Telemetry-Instrumentation System for Monitoring Multiple Subcutaneously Implanted Glucose Sensors", IEEE Transactions on Biomedical Engineering, vol. 41, No. 10, Oct. 1994.
Yu, et al., "A long-term flexible minimally-invasive implantable glucose biosensor based on an epoxy-enhanced polyurethane membrane", Biosensors and Biolectronics 21 (2006).
Allen, et al., 4H—SiC MESFET's on high resistivity substrates with 30 GHz fmax, 53rd annual device research conference digest, 1995.
Chiu, et al., An Implantalbe Multifuncational needle type biosensor with integrated RF capability; Proceedings of the 2005 IEEE, Engineering in Medicine and Biology 27th Annual Conference, Sep. 1-4, 2005.
Coletti, et al., Biocompatibility and wettability of crystalline SiC and Si surfaces, Proceedings of the 29th Annual International Conference of the IEEE EMBS, Aug. 23-26, 2007.
He, et al., Improvement of Integrated Dipole Antenna Performance Using Diamond for Intra-Chip Wireless Interconnection, IEEE, 2010.
Renard, E., Implantable glucose sensors for diabetes monitoring; Department of Endocrinology, Min Invas Ther & Allied Technol, 2004.
Santavira, et al., Biocompatibility of silicon carbide in colony formation test in vitro, A promising new ceramic THR implant coating material, Arch Orthop Trauma Surg, 1998.
Sriram, et al., 4H—SiC MESFETTs with 42 GHz fmax, IEEE Electron Device Letters, vol. 17, No. 7, Jul. 1996.
Tucker, et al., Fully ion implanted MESFETs in bulk semi-insulating 4H—SiC, Diamond and Related Materials, 11, 2002.
Voskerician, et al., Biocompibility and biofouling of MEMS drug delivery devices, Elsevier Science, Ltd., Biomaterials 24, 2003.
Watanabe, et al., Effect of high-resistivity Si Substrate on Antenna Transmission Gain for On-Chip Wireless Interconnects, Japanese Journal of Applied Physics, vol. 43, No. 4B, 2004.
Wilkins, et al., Integrated Implantable device for long-term glucose monitoring, Biosensors & Bioelectronics 10, 1995.
Chandler, et al., Intraoperative use of real-time ultrasonography in neurosurgery, J. Neurosurg, vol. 57, Aug. 1982.
Dohramann, et al., Use of Ultrasound in Neurosurgical Operations: A Preliminary Report, Brown and Company, 1981.
Dhormann, et al., Intraoperative Ultrasound Imaging of the Spinal Cord: Syringomyelia, Cysts, and Tumors—A Preliminary Report, Brown and Company, 1982.
Hammoud, et al., Use of intraoperative ultrasound for localizing tumors and determining the extent of resection: a comparative study with magnetic resonance imaging; J. Neurosurg 84:737-741, 1996.
Saddow, et al., Advances in Silicon Carbide Processing and Applications; ISBN1-58053-740-5, 2014.
Afroz, et al., "Bio-Compatible Material for Implantable RF Antenna", Depart of EE, USF ORS Research One 2010.
Afroz, et al., Bio-compatible Material for Implantable RF Antenna; Dept of EE, USF Research One 2010.
Karacolak T et al: "Design of a Dual-Band Implantable Antenna and Development of Skin Mimicking Gels for Continuous Glucose Monitoring", IEEE Transactions on Microwave Theory and Techniques, vol. 56, No. 4, Apr. 4, 2008 (Apr. 4, 2008), pp. 1001-1008, XP011205837, IEEE Service Center, Piscataway, NJ, US ISSN: 0018-9480 p. 1003, col. 2, line 12—p. 1004, col. 1, line 12; figures 1,9.
Mahboobeh Mahmoodi and Li da Ghazanfari: "Fundamentals of biomedical applications of biomorphic SiC" In: Edited by Prof. Rosario Gerhardt: "Properties and Applications of Silicon Carbide", Apr. 4, 2011 (Apr. 4, 2011), InTech, XP002697629, ISBN: 978-953-307-201-2 pp. 297-344, p. 303, lines 28-42.
Shamima Afroz, Sylvia W Thomas, Gokhan Mumcu, Christopher W Locke, Stephen E Saddow: "A Biocompatible SiC RF Antenna for In-Vivo Sensing Applications, abstr. nr. mrssl2-1433-h06-05", Mater. Res. Soc. Symp. Proc., vol. 1433, Jun. 15, 2012 (Jun. 15, 2012), XP002697628, DOI: 10.1557/opl.2012.1150 the whole document.
International Search Report and Written Opinion, dated Jun. 28, 2013.

* cited by examiner

IMPLANTABLE BIOCOMPATIBLE SIC SENSORS

CROSS-REFERENCE TO RELATED APPLICATION

This application is the 35 U.S.C. § 371 national stage of, and claims priority to and the benefit of, PCT application PCT/US2013/030362, filed Mar. 12, 2013, which claims priority to and the benefit of U.S. Provisional Application No. 61/609,546, filed on Mar. 12, 2012, herein incorporated by reference in its entirety.

BACKGROUND

In recent years, considerable progress has been made in developing implantable biosensors that can continually monitor different health care issues, such as glucose levels of a diabetic patient. However, to be truly beneficial, the implanted sensor must be able to function properly for an extended period of time. The biosensors developed thus far typically can only remain functional up to 10-30 days after their implantation in the body. Contributing factors for this loss of functionality include the degradation and fouling of the sensor and the changes in the tissue surrounding the sensor such as fibrosis and inflammation. While researchers explore potential solutions to improve the current implantable biosensors, there is an urgent need to investigate alternative technologies and materials of choice.

BRIEF DESCRIPTION OF THE DRAWINGS

The present disclosure may be better understood with reference to the following figures. Matching reference numerals designate corresponding parts throughout the figures, which are not necessarily drawn to scale.

DETAILED DESCRIPTION

As described above, there is a need for implantable biosensors that can remain functional in vivo for extended periods of time. Disclosed herein are implantable biosensors that can remain functional for much longer than current designs, potentially many years. In some embodiments, the biosensors include a sense antenna that is constructed out of silicon carbide.

In the following disclosure, various embodiments are described. It is to be understood that those embodiments are example implementations of the disclosed inventions and that alternative embodiments are possible. All such embodiments are intended to fall within the scope of this disclosure.

The disclosed biosensors comprise small implantable antennas that can be used for continuous monitoring and sensing. A central theme for the biosensors is that an implantable radio frequency (RF) antenna fabricated with biocompatible material is well suited for long term in vivo systems. A particular example would be a reliable continuous glucose monitoring system able to control hypoglycemia, thereby lessening the complications associated with diabetes.

Many biomedical devices require materials that are both biocompatible and have sensing capability. Biochemical sensors, biologically-interfaced neural networks, and smart biomedical implants require semiconductor materials so that sensing can be performed using not only mechanical means but also electrical means, as well as micro-electro-mechanical systems (MEMS). To date, the biocompatibility of only a few crystalline semiconductors has been investigated, with silicon (Si) and titanium dioxide ($TiO_2$) drawing most of the attention. Unfortunately, Si has been shown to display cytotoxicity, mostly due to its instability in aqueous solutions with subsequent formation of silica and silicates, which are known to be harmful to cells. Furthermore, $TiO_2$, which can become a semiconductor upon ion implantation, does not display sufficiently satisfying electronic properties that may justify its adoption for sensing applications.

Silicon carbide (SiC), on the other hand, is a semiconductor that is chemically inert to acids, alkalis, and salts, does not expand in liquid environments, and can be processed with the existing methods developed for the silicon industry. SiC displays biocompatibility, longevity, and great sensing potentiality. SiC's chemical inertness, superior tribological properties, and hemocompatibility make it a very promising candidate for in vitro and in vivo biosensors, biologically-interfaced neural networks, and intelligent implantable medical devices. As described herein, SiC can be used to construct a fully implantable, long-term, continuous monitoring RF antenna sensor that can remain functional in the body for years and that does not require protective encasing. By way of example, such an antenna can be used for continuous glucose monitoring. Another application is use of the antenna as a communicating device to other implantable sensors using telemetry unit integration.

Figure 1:
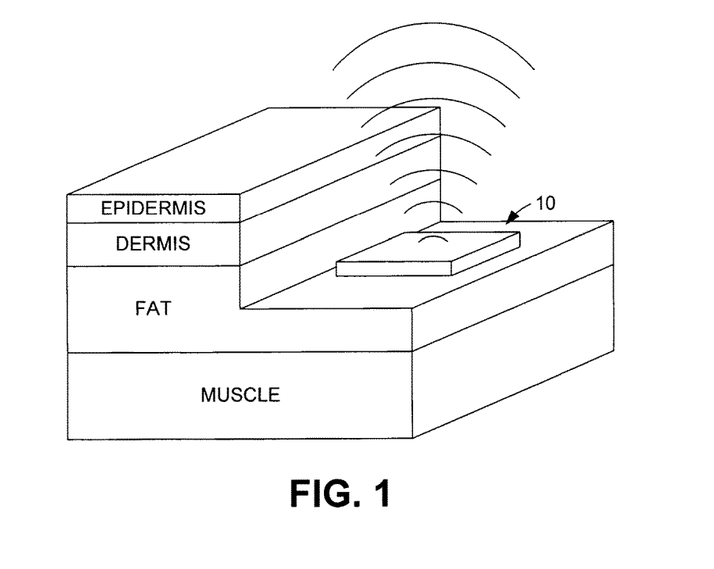
FIG. 1 is a schematic view of a biosensor implanted beneath the skin.

FIG. 1 schematically illustrates a subcutaneously implanted biosensor 10. In particular, the biosensor 10 is shown implanted within the fat layer between the muscle and the dermis. In this position, the biosensor 10 can sense a given body parameter, such as blood glucose levels, and wirelessly transmit the results to a separate device, such as a handheld, notebook, or desktop computer.

Figure 2:
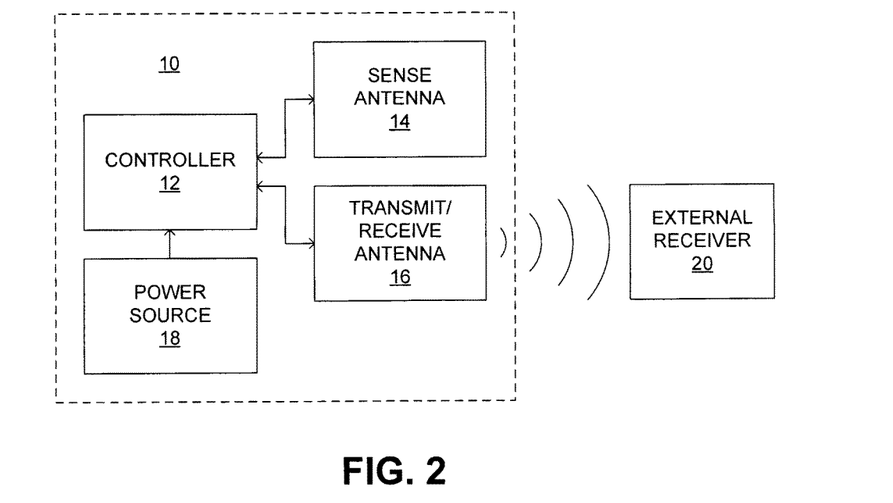
FIG. 2 is a block diagram showing example components of the biosensor of FIG. 1.

FIG. 2 illustrates example components of the biosensor 10. As is shown in FIG. 2, the biosensor 10 comprises a controller 12, a sense antenna 14, a transmit/receive antenna 16, and a power source 18. In operation, the controller 12, operating under power provided by the power source 18 (e.g., a battery), drives the sense antenna 14 with a known input signal. In some embodiments, the sense antenna 14 operates at approximately 402 MHz. The transmitted signal is reflected by the biomaterial surrounding the biosensor 10 and is received by the sense antenna 14. The frequency of the reflected signal is then sensed by the controller 12. Because changes in the material in which the biosensor 10 is implanted alter the radiation frequency of the antenna 14, the body parameter can be determined from the observed frequency. For example, changes in blood glucose levels alter the peak radiation frequency of the sense antenna 14.

The peak radiation frequency value can then be wirelessly transmitted to an external receiver 20 of the other device (e.g., handheld, notebook, or desktop computer) using the transmit/receive antenna 16 to provide an indication of the body parameter to the patient or the patient's caregiver. In some embodiments, the transmit/receive antenna 16 operates at approximately 2.4 GHz.

Figure 3:
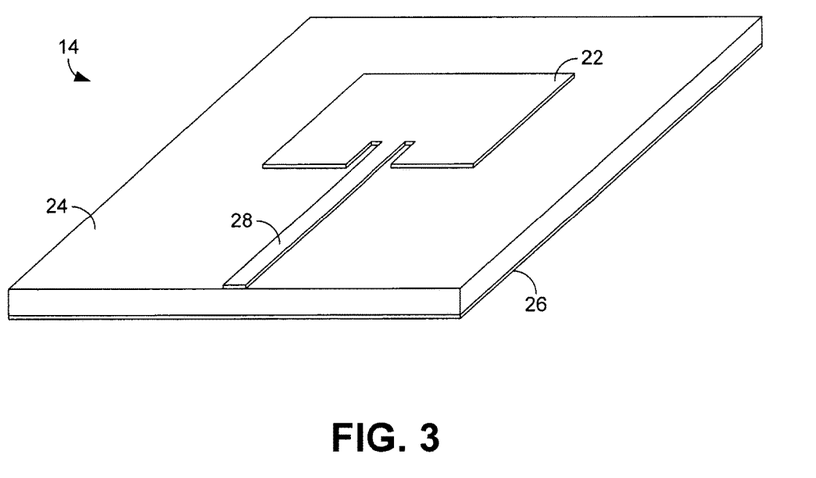
FIG. 3 is a perspective view of an embodiment of an antenna that can be used in the biosensor of FIG. 2.

FIG. 3 illustrates an example configuration for the sense antenna 14. In the example of FIG. 3, the antenna 14 is configured as a rectangular microstrip antenna, commonly referred to as a patch antenna. The antenna 14 comprises a radiating electrode 22 configured as a flat rectangular patch, which is formed on a top side of a substrate 24. The substrate 24 is, in turn, provided on a ground plane 26. Extending from the electrode 22 along the top side of the substrate 24 is a feed line 28, which can be made of the same material as the electrode.

FIGS. 4-8 illustrate example constructions for the patch antenna shown in FIG. 3. Beginning with FIG. 4, a first antenna construction 30 comprises a ground plane 32, a substrate 34, a seed layer 36, and an electrode 38. In some embodiments, the ground plane 32 comprises Ti/Au or heavily-doped poly 3C-SiC, the substrate 34 comprises semi-insulating, single-crystal silicon carbide such as 4H-SiC, the seed layer 36 comprises polysilicon, and the electrode 38 comprises highly-doped, polycrystalline silicon carbide (poly-SiC). In some embodiments, the ground plane 32 is approximately 0.1 to 0.2 microns (μm) thick, the substrate 34 is approximately 375 to 750 μm thick, the seed layer 36 is approximately 50 to 150 Angstroms (Å) thick, and the electrode 38 is approximately 0.5 to 3 μm thick. As a specific example, the ground plane 32 can be approximately 0.1 μm thick, the substrate 34 can be approximately 375 μm thick, the seed layer 36 can be approximately 100 Å thick, and the electrode 38 can be approximately 2 μm thick.

Figure 4:
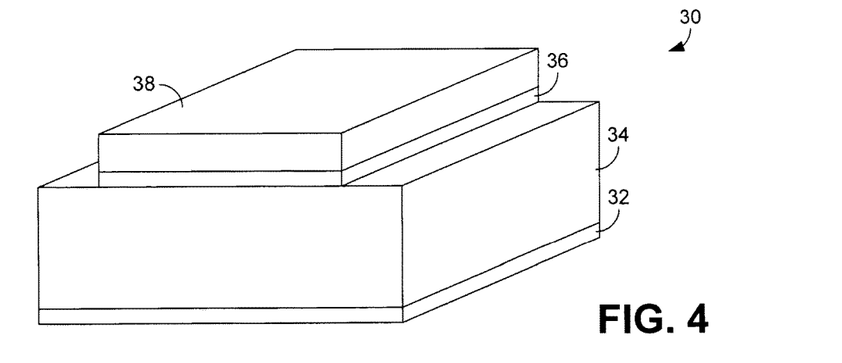
FIG. 4 is a perspective view of a first example construction of the antenna of FIG. 3.

The antenna 30 can be constructed using an etch-back process involving highly doped 3C-SiC epitaxial growth and patterning. In one embodiment, a 4H-SiC substrate is first cleaned. Next, a layer of polysilicon is deposited using, for example, a low pressure CVD (LPCVD) in a tube furnace. Once the polysilicon has been deposited, poly 3C-SiC is grown on the polysilicon using a low pressure, high temperature CVD process. The poly 3C-SiC can be grown in the presence of a hydrogen carrier gas with silane gas and propane gas as the growth precursors, and nitrogen gas can be used as a dopant. Once the various layers have been formed, standard photolithography and an appropriate mask can be used to form the shape of the electrode 22 shown in FIG. 3. By way of example, deep reactive ion etching (DRIE) can be used to pattern the poly 3C-SiC electrode in the semiconductor material.

Figure 5:
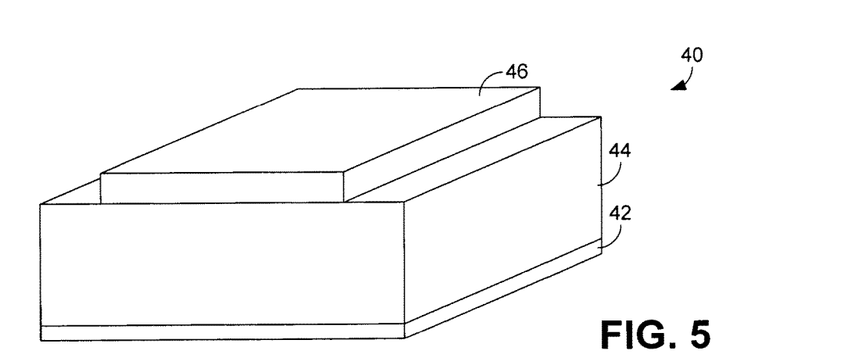
FIG. 5 is a perspective view of a second example construction of the antenna of FIG. 3.

Referring next to FIG. 5, an antenna 40 comprises a ground plane 42, a 4H-SiC semi-insulating substrate 44, and a highly-doped 4H-SiC homo-epitaxial layer 46 grown on the substrate using CVD. The 4H-SiC can be doped n-type using nitrogen gas and, in some embodiments, can be grown using hot-wall CVD. One of the benefits of SiC growth via hot-wall CVD is the high temperature processing flexibility. Not only can the CVD reactor operate at high processing temperatures (in excess of 2,000° C.), but an identical design, with different mechanical components, can be used for lower temperature processing where flow rates and other parameters are adjusted. After growing the highly doped epilayer, the antenna 40 is etched using a designed antenna mask. The patterned doped layer 46 acts as the top-side electrode (i.e., conductive radiating patch element).

Figure 6:
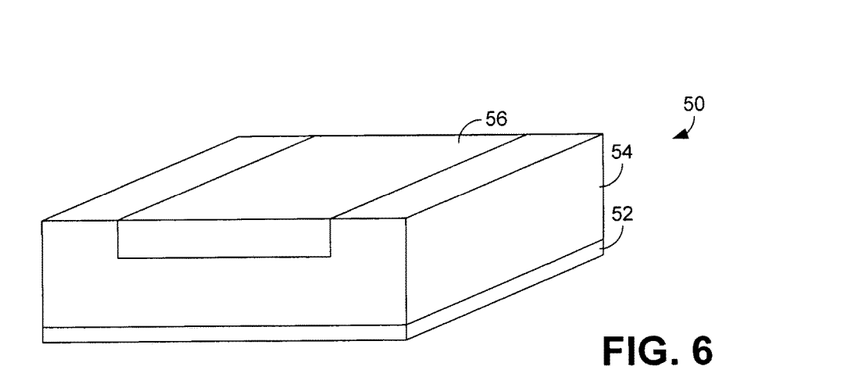
FIG. 6 is a perspective view of a third example construction of the antenna of FIG. 3.

FIG. 6 shows a fully planar implementation in which the antenna 50 comprises a ground plane 52 and a semi-insulating 4H-SiC substrate 54 formed on the ground plane. Ion implantation is applied to the SiC material to obtain a heavily doped antenna region with metal-like conductivity. After patterning on the surface an antenna mask using a dense metal such as Ni, ion-implantation is applied on the substrate 54 at a high enough energy to synthesize a degenerate SiC layer to form an antenna electrode 56. A CVD reactor can be used to anneal ion-implanted SiC at high temperatures.

Figure 7:
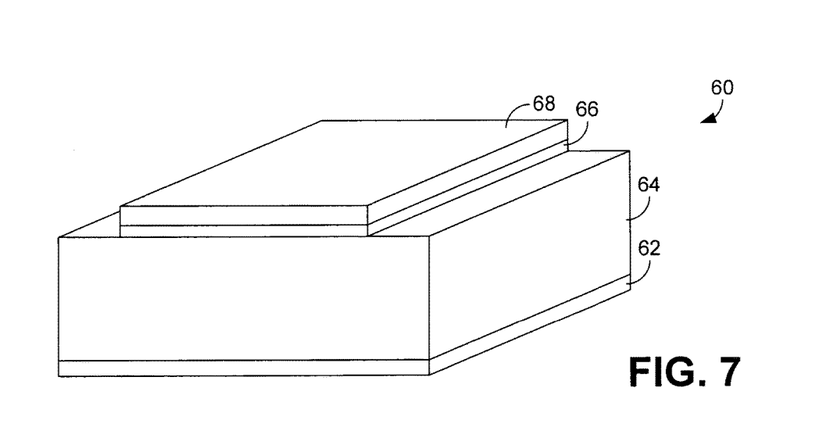
FIG. 7 is a perspective view of a fourth example construction of the antenna of FIG. 3.

FIG. 7 illustrates an antenna 60 that comprises a ground plane 62, a 4H-SiC substrate 64, a layer of titanium (Ti) 66 formed on the substrate, and a layer of gold (Au) 68 formed on the Ti layer. The Ti layer 66 is used as an adhesive layer for the Au layer 68 and therefore can be very thin, for example, 500 Angstroms thick. The Au layer, which acts as the electrode, can be, for example, approximately 0.45 μm thick.

Figure 8:
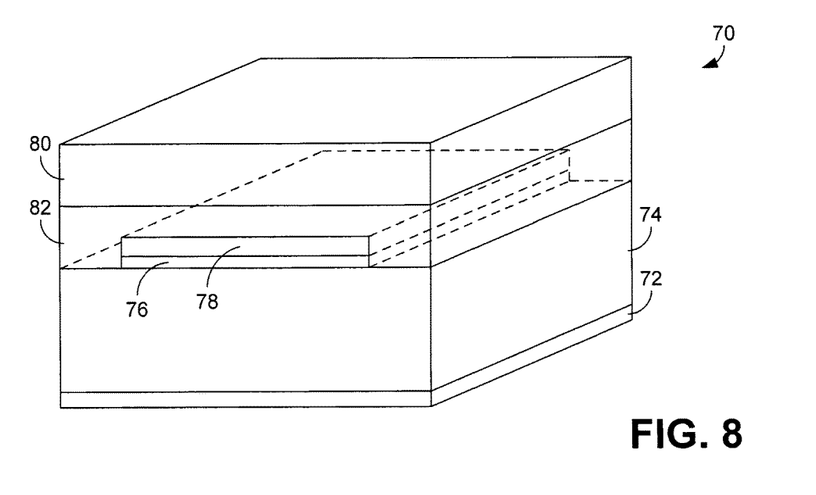
FIG. 8 is a perspective view of a fifth example construction of the antenna of FIG. 3.

FIG. 8 illustrates an antenna 70 that is similar to the antenna 60 shown in FIG. 7. Accordingly, the antenna 70 includes a ground plane 72, a 4H-SiC substrate 74, a Ti layer 76, and a Au layer 78. In addition, however, the antenna 70 further includes a layer of polyethylene glycol (PEG) 80 that acts as a protein inhibitor to make the antenna more biocompatible. As is further shown in FIG. 8, a layer of $SiO_2$ 82 is used between the PEG layer 80 and the remainder of the antenna 70 to covalently bond the PEG layer in place.

A microstrip patch antenna of the type described above was fabricated and tested to demonstrate the feasibility of a biocompatible SiC-based implantable sensor for continuous glucose monitoring. Patch antennas are low profile, inexpensive to manufacture, compatible with MMIC designs, and versatile in terms of resonant frequency, polarization, radiation pattern, and impedance. There are numerous techniques available for the miniaturization of patch antennas.

Figure 9:
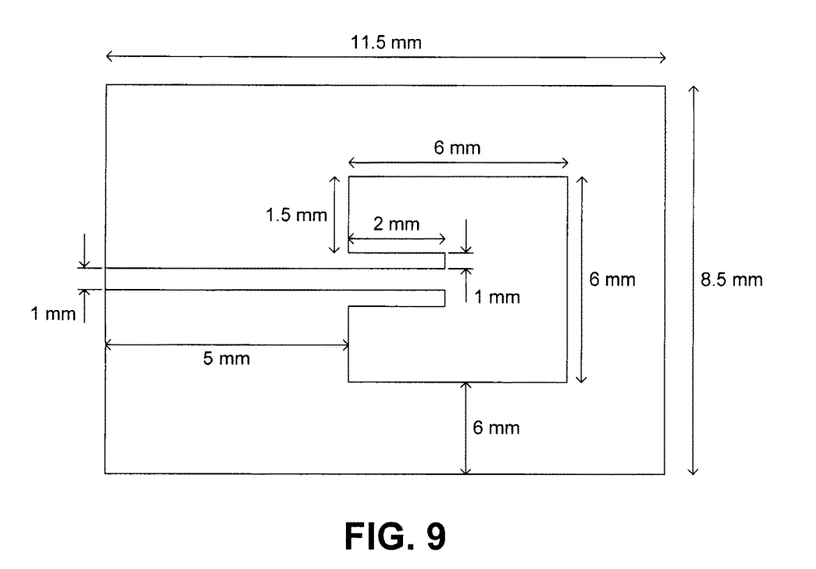
FIG. 9 is schematic drawing of an antenna that was fabricated for testing purposes.

A conventional rectangular patch antenna having a design frequency of 10 GHz was selected to minimize the size and associated substrate costs. The configuration and dimensions of the antenna are shown in FIG. 9. As shown in that figure, the antenna layout is 8.5×11.5 mm$^2$ on a 0.37 mm thick semi-insulating bio-compatible 4H-SiC substrate ($\varepsilon_r$=10) that is known to exhibit very low microwave loss. After the substrate was cleaned using a standard RCA sequence, the antenna was metallized with titanium/gold (Ti/Au) using an electron-beam evaporator and then patterned with standard photolithography. The inlet feed length was selected to allow for proper impedance matching. The geometrical design parameters were determined based on numerical simulations using the Ansys High Frequency Structure Simulator (HFSS) tool. The simulated radiation efficiency in free space was 65%. Also, the simulated broadside realized gain was 3.94 dB.

It is important to note that minerals, such as calcium, chloride, potassium, and magnesium, are also present in the blood. For diabetic patients, the concentration of these minerals has been shown to vary insignificantly. Therefore, the variation in blood permittivity becomes strongly dependent on the glucose level. When the antenna is placed near the blood vessel, the permittivity varies with blood glucose, altering antenna parameters such as the input impedance and reflection coefficient $S_{11}$. These changes can therefore be utilized to directly estimate the patient's plasma glucose levels.

The operational position of the disclosed implantable sensor was selected within a fatty tissue region that is in close proximity to a blood vessel. Therefore, fatty tissue and blood-mimicking liquids were synthesized for in vitro testing. The fatty tissue mimicking liquid was prepared by mixing oil and dibutyl glycol ether (DBGE). The permittivity and conductivity of the liquid was measured by using an HP 85070A dielectric probe kit connected to an HP 8719D vector network analyzer (VNA). The final recipe for the fatty tissue-mimicking liquid, shown in Table I, was determined by adjusting the ratio of oil and DBGE.

TABLE I

Receipt For Realizing Fat Mimicking Liquid at 10 GHz

| | |
|---|---|
| Oil | 10.2% |
| DGBE (Diethylene Glycol Butyl Ether) | 89.8% |

Figure 10:
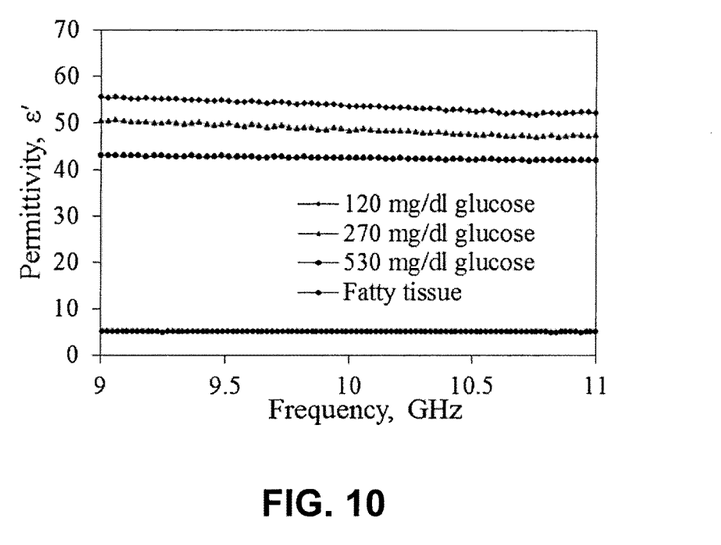
FIG. 10 is a graph that plots measured permittivity of fat- and blood-mimicking liquids with varying glucose levels within the blood.

The measured properties of human fatty tissue (fat) were taken from the literature. FIG. 10 shows the measured real part of the permittivity for fat mimicking liquid as $\varepsilon_r \approx 5$ and this is in accordance with the values reported in the literature. The corresponding conductivity was calculated from the measured imaginary part of the permittivity as $\sigma \approx 0.51$ S/m. The synthetic body fluid (SBF), or acellular human blood plasma-mimicking liquid, was prepared by dissolving the appropriate quantities of nine separate chemicals in de-ionized water. Different weights of D-glucose were added to the blood-mimicking liquid in order to represent various glucose levels as shown in Table II. The accuracy of the glucose levels was verified using a conventional glucometer (TRUEtrack blood glucose monitoring system). FIG. 10 also demonstrates the measured real part of the permittivity from the blood mimicking liquids carrying different glucose concentrations. As expected, the permittivity varies with glucose levels. In addition, the corresponding conductivities were calculated from the measured imaginary part of the permittivity as 18 S/m, 15 S/m and 13 S/m for the blood-mimicking liquids exhibiting 120 mg/dl, 270 mg/dl, and 530 mg/dl glucose concentrations, respectively.

TABLE II

D-Glucose Weight vs. Glucose Concentration

| Glucose concentration (mg/dl) | D-Glucose (grms) |
|---|---|
| 127 | 0.021 |
| 270 | 0.039 |
| 530 | 0.082 |

Figure 11:
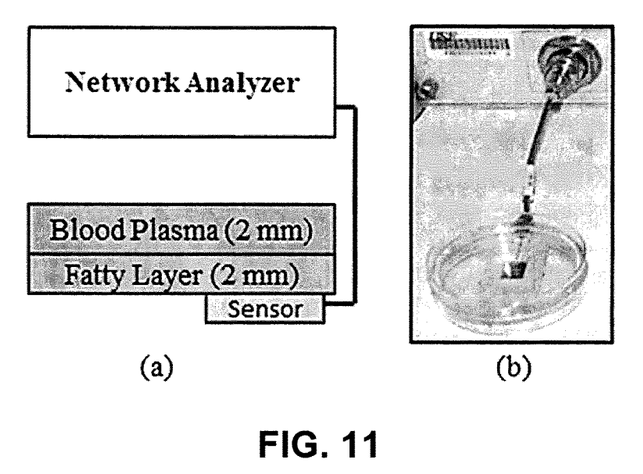
FIGS. 11(a) and 11(b) are a schematic drawing and a photograph, respectively, of an experimental setup for measuring blood plasma glucose levels.
Figure 12:
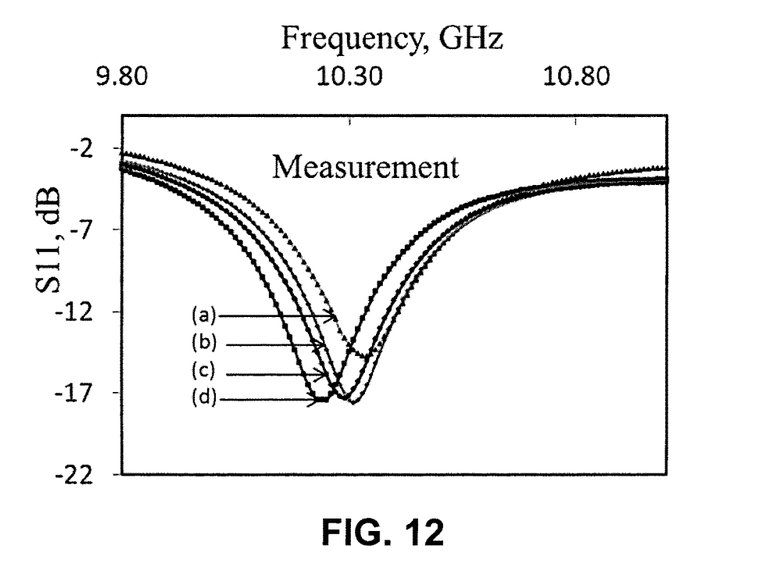
FIG. 12 is a graph of measured and simulated $S_{11}$ response of the antenna of FIG. 9 as a function of the glucose concentration within blood at (a) 0 mg/dl (no glucose added), (b) 120 mg/dl, (c) 270 mg/dl, and (d) 530 mg/dl.
Figure 13:
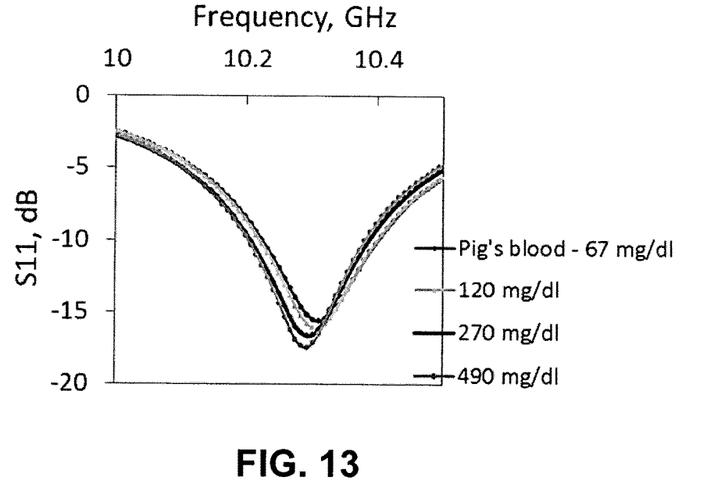
FIG. 13 is a graph of measured $S_{11}$ response of the antenna of FIG. 9 as a function of glucose concentration with pig blood at (a) 67 mg/dl, (b) 120 mg/dl, (c) 270 mg/dl, and (d) 490 mg/dl.

The antenna sensor was tested via reflection coefficient measurements carried out using the HP 8719D VNA. FIG. 11 depicts the experimental setup that was utilized to model the antenna placed inside a fatty layer in close proximity to blood. The thicknesses of the fatty-tissue-and blood-mimicking liquid layers were 2 mm each and their volume was 5 ml. The baseline reading (i.e., the resonance frequency at which the antenna's input reflection coefficient $S_{11}$ displays a minimum) from the sensor was taken by using blood-mimicking liquid with zero glucose concentration. Following this, three blood-mimicking liquids exhibiting different glucose concentrations were utilized within the experimental setup to sequentially observe the variation in the resonance frequency of the antenna. Specifically, as shown in FIG. 12, the measured shift in the resonance frequency was towards lower frequency by as much as 40 MHz for the largest glucose concentration of 530 mg/dl. This implies a 97 KHz shift per 1 mg/dl change in blood glucose. The simulated $S_{11}$ response of the antenna using the measured permittivity values of the fat- and blood-mimicking liquids was found to be in good agreement with the experimental results. The sensor's performance was also demonstrated using pig blood. Initially, the pig blood had a glucose level of 67 mg/dl. Three additional samples were prepared with glucose levels of 120 mg/dl, 270 mg/dl, and 490 mg/dl by adding D-glucose to the blood. Similar to the glucose-sensing experiment using blood-mimicking liquid, the glucose levels were measured using pig blood. The sensor response is shown in FIG. 13.

Figure 14:
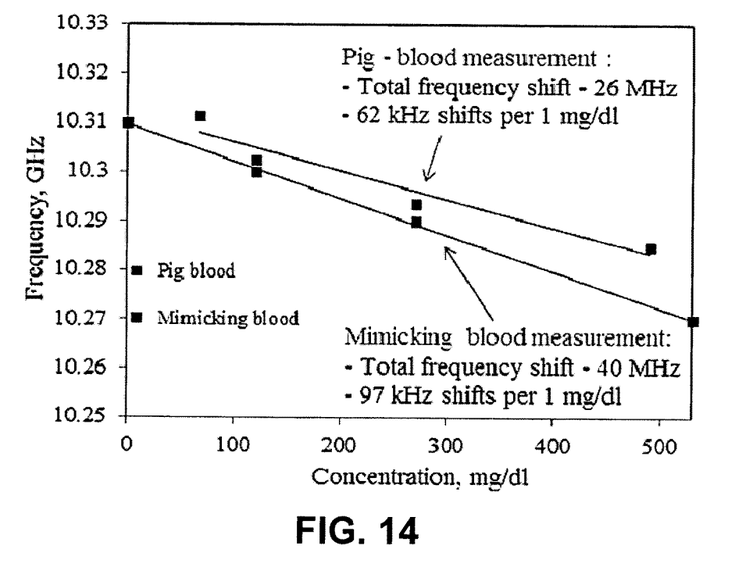
FIG. 14 is a graph of measured linear response of a sensor wherein frequency shifting is a direct function of glucose concentration.

FIG. 14 shows the resonance frequency of the antenna measured at multiple glucose levels. It is seen that the response is almost linearly dependent on the glucose concentration both for the blood-mimicking liquid and the pig blood.

The invention claimed is:

1. An implantable subcutaneous blood glucose level biosensor comprising:
   a controller configured to generate a known input signal;
   a sense antenna controlled by the controller that is configured to transmit the known input signal into surrounding biomaterial and receive a reflected peak radiation frequency signal from the surrounding biomaterial that is indicative of a blood glucose level within the biomaterial, the sense antenna being a patch antenna comprising a semi-insulating single-crystal silicon carbide substrate composed of 4H-SiC, a radiating electrode comprising a flat rectangular silicon carbide patch formed on a first side of the semi-insulating single-crystal silicon carbide substrate, a feed line extending across the first side of the semi-insulating single-crystal silicon carbide substrate to the radiating electrode, and a ground plane formed on a second side of the semi-insulating single-crystal silicon carbide substrate, wherein the sense antenna is not encased in protective material;
   a transmission antenna configured to transmit the reflected peak radiation frequency signal to an external device; and
   a power source that provides power to the controller.

2. The implantable biosensor of claim 1, wherein the radiating electrode is composed of doped polycrystalline silicon carbide.

3. The implantable biosensor of claim 1, wherein the radiating electrode is composed of doped 3C-SiC.

4. The implantable biosensor of claim 3, wherein the sense antenna further comprises a polysilicon seed layer provided between the radiating electrode and the silicon carbide substrate.

5. The implantable biosensor of claim 1, wherein the radiating electrode is a doped 4H-SiC homo-epitaxial layer.

6. The implantable biosensor of claim 1, wherein the radiating electrode comprises ion-implanted 4H-SiC.

\* \* \* \* \*